United States Patent
Beato et al.

(10) Patent No.: US 10,709,691 B2
(45) Date of Patent: Jul. 14, 2020

(54) PHARMACEUTICAL DOSAGE FORMS

(71) Applicant: RECORDATI AG, Baar (CH)

(72) Inventors: Stefania Beato, Basel (CH); Peggy Quinton, Waldighoffen (FR)

(73) Assignee: RECORDATI AG, Baar (CH)

(*) Notice: Subject to any disclaimer, the term of this patent is extended or adjusted under 35 U.S.C. 154(b) by 98 days.

(21) Appl. No.: 16/175,082

(22) Filed: Oct. 30, 2018

(65) Prior Publication Data
US 2019/0060283 A1 Feb. 28, 2019

Related U.S. Application Data

(63) Continuation of application No. 15/323,991, filed as application No. PCT/IB2015/055098 on Jul. 6, 2015, now Pat. No. 10,143,680.

(60) Provisional application No. 62/021,271, filed on Jul. 7, 2014.

(51) Int. Cl.
*A61K 31/4188* (2006.01)
*A61K 9/20* (2006.01)
*A61K 31/4184* (2006.01)
*A61K 9/28* (2006.01)

(52) U.S. Cl.
CPC ........ *A61K 31/4188* (2013.01); *A61K 9/2009* (2013.01); *A61K 9/2036* (2013.01); *A61K 9/2054* (2013.01); *A61K 9/2095* (2013.01); *A61K 9/2813* (2013.01); *A61K 9/2826* (2013.01); *A61K 9/2866* (2013.01); *A61K 31/4184* (2013.01)

(58) Field of Classification Search
CPC .............. A61K 31/4188; A61K 9/2866; A61K 9/2826; A61K 9/2813; A61K 9/2009; A61K 9/2095; A61K 9/2036; A61K 31/45; A61K 9/2054
See application file for complete search history.

(56) References Cited

U.S. PATENT DOCUMENTS

| | | | |
|---|---|---|---|
| 2008/0269343 A1 | 10/2008 | Rigassi-Dietrich et al. | |
| 2010/0105710 A1* | 4/2010 | Murakawa | A61K 31/513 514/274 |
| 2012/0064157 A1 | 3/2012 | Dokou et al. | |

FOREIGN PATENT DOCUMENTS

| | | |
|---|---|---|
| EP | 2815749 A1 | 12/2014 |
| WO | WO2007/024945 A1 | 3/2007 |
| WO | WO2011088188 A1 | 7/2011 |
| WO | WO2013109514 A1 | 7/2013 |
| WO | WO2013/126326 A1 | 8/2013 |
| WO | WO2013153129 A1 | 10/2013 |

OTHER PUBLICATIONS

"Handbook of Pharmaceutical Excipients"; Fifth Ed. Edited by Raymond C Rowe et al.; ISBN 978-0-85369-618-6, p. 120-123, 132-135, 188-191, 430-433, 449-453-3Dec. 31, 2006.
Hu Shigao et al., "Progress of Drug-excipients Compatibility in Oral Solid Dosage Forms", Chin JMAP, Sep. 2012, vol. 29, No. 9, p. 789-793, Sep. 30, 2012.
Boscaro et al., "Treatment of Pituitary-Dependent Cushing's Disease with the Multireceptor Ligand Somatostatin Analog Pasireotide (SOM230): A Multicenter, Phase II Trial", J Clin Endocrinal Metab, vol. 94, pp. 115-122, Jan. 1, 2009.

* cited by examiner

*Primary Examiner* — Sudhakar Katakam
(74) *Attorney, Agent, or Firm* — Hueschen and Sage

(57) ABSTRACT

The present invention relates to pharmaceutical dosage forms for oral administration comprising the drug substance 4-[(5R)-6,7-dihydro-5H-pyrrolo[1,2-c]imidazol-5-yl]-3-fluorobenzonitrile or any pharmaceutically acceptable salt thereof and to processes of making said solid pharmaceutical dosage forms.

5 Claims, No Drawings

PHARMACEUTICAL DOSAGE FORMS

FIELD OF THE INVENTION

The present invention relates to pharmaceutical dosage forms for oral administration comprising the drug substance 4-[(5R)-6,7-dihydro-5H-pyrrolo[1,2-c]imidazol-5-yl]-3-fluorobenzonitrile or any pharmaceutically acceptable salt thereof. It further relates to processes of making said solid pharmaceutical dosage forms.

BACKGROUND OF THE INVENTION

The compound 4-[(5R)-6,7-dihydro-5H-pyrrolo[1,2-c]imidazol-5-yl]-3-fluorobenzonitrile and a method of its preparation were disclosed in WO2007/024945 the content thereof is incorporated by reference herein. Said compound is represented by formula (1) and is herein referred to as drug substance or compound of formula (1).

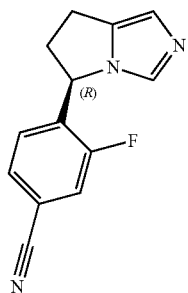

(1)

Compound of formula (1) has adrenal hormone-modifying properties and may be used for treating a disease or disorder characterised by increased stress hormone levels and/or decreased androgen hormone levels in a subject, by administering to the subject a therapeutically effective amount of a compound of formula (1) or a pharmaceutically acceptable salt thereof.

Further, compound of formula (1) may be used for treating heart failure, cachexia, acute coronary syndrome, chronic stress syndrome, Cushing's syndrome or metabolic syndrome, comprising administering to the subject a therapeutically effective amount of a compound represented by formula (I) or a pharmaceutically acceptable salt thereof.

Said medical uses of compound of formula (1) were described in WO2011/088188 the content thereof is incorporated by reference herein.

Several crystalline and amorphous forms of the compound of formula (1) and methods to preparing said forms were described in WO2013/109514 the content thereof is incorporated by reference herein.

However, specific pharmaceutical compositions or pharmaceutical dosage forms to deliver the compound of formula (1) to patients were not described so far.

SUMMARY OF THE INVENTION

As every API has its own physical, chemical and pharmacological characteristics, a suitable pharmaceutical composition and dosage form has to be individually designed for every new API.

The design of a pharmaceutical composition, a pharmaceutical dosage form as well as a commercially viable pharmaceutical manufacturing process for the compound of formula (1) is especially difficult for (inter alia) the following reasons:

Said compound, especially in its phosphate salt form, is very cohesive and is therefore affected by a strong tendency to aggregation. This aggregation was found to be responsible for poor and inhomogeneous drug substance distribution within the blend with other ingredients.

Further, said drug substance was experienced to be of poor pharmaceutical processability. For example, it was experienced to be non-sievable and poorly flowable (ffc 1.1).

Said compound, especially in its phosphate salt form, has a very low drug substance bulk density (0.1-0.3 g/mL) which is associated with problems of poor processability, e.g. poor flow, and the need for special compaction steps in the manufacturing with the aim to formulate said compound into a oral dosage form of reasonable size for the convenience of patients which have to swallow the resulting drug product.

Mainly due to its amine function, said compound is also affected by chemical instabilities, and incompatibilities with other ingredients.

In addition, said drug substance, especially in its phosphate salt form, is hygroscopic which again is associated with stability issues.

It is therefore difficult to design a pharmaceutical composition for compound of formula (1) which is pharmaceutically processably and to design a pharmaceutical dosage form that is stable and of an acceptable size to be easily swallowable. It is moreover difficult to design a manufacturing process which allows the compound of formula (1) to be reliably produced at a commercially viable scale into pharmaceutical dosage forms which meets the high quality standards of medicines for humans a at commercial scale.

One of the difficulties was to identify suitable filler. There are basically three fillers which are predominantly used in the pharmaceutical field: lactose, mannitol, and microcrystalline cellulose (MCC). However, the use of lactose as filer was found to cause chemical degradation products after compressing compound of formula (1) to tablets. The use of mannitol as intragranular filler caused stickiness issues and ribbon discoloration during compaction steps. The use of MCC was regarded as not suitable as filler for the compound of formula (1) as MCC is known to be associated to drug substance absorption effects due to its amorphous regions. As MCC has a negatively charged surface, the absorption effects are especially problematic for cationic drugs such as compound of formula (1). Also in this respect, the low bulk density (which corresponds with a high surface area) of the cationic compound of formula (1) is problematic and makes the compound even more prone to absorption effects. Especially, at low dosage strength said absorption effects can cause a significant loss of drug availability. Consequently, all established filers had to be disregarding for the design of a pharmaceutical composition and pharmaceutical dosage form of compound of formula (1).

In view of the above mentioned difficulties and considerations it was surprising that the present inventors found in counter-intuitive trials that the use of MCC as filler for dosage forms of compound of formula (1) is possible. It was further surprisingly found that by blending compound of formula (1) together with MCC turned the problematically very cohesive drug substance into a very well pharmaceutically processable blend.

Taking these surprising findings into account, the inventors herewith provide the present invention in its following aspects.

In accordance with a first aspect of the invention, there is provided a pharmaceutical dosage form for oral administration comprising
(a) the drug substance 4-[(5R)-6,7-dihydro-5H-pyrrolo[1,2-c]imidazol-5-yl]-3-fluorobenzonitrile as defined by formula (1)

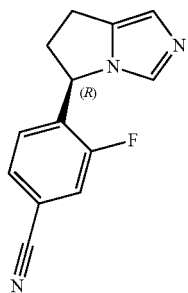

or any pharmaceutically acceptable salt thereof, and
(b) at least 30% by weight of microcrystalline cellulose based on the total weight of said pharmaceutical dosage form.

In accordance with a second aspect of the invention, there is provided a process for the preparation of said pharmaceutical dosage form comprising blending the drug substance 4-[(5R)-6,7-dihydro-5H-pyrrolo[1,2-c]imidazol-5-yl]-3-fluorobenzonitrile with microcrystalline cellulose.

In accordance with a third aspect of the invention, there is provided a pharmaceutical dosage form obtainable by said process.

DETAILED DESCRIPTION OF THE INVENTION

Herein alter, the present invention is described in further detail and is exemplified.

In the aspects of the present invention the drug substance 4-[(5R)-6,7-dihydro-5H-pyrrolo[1,2-c]imidazol-5-yl]-3-fluorobenzonitrile, herein also referred to as compound of formula (1), is present as (R)-enantiomer of 4-[6,7-dihydro-5H-pyrrolo[1,2-c]imidazol-5-yl]-3-fluorobenzonitrile. However, it may be also present as (S)-enantiomer of said compound, or as mixture of said enantiomers. Preferably said drug substance is present as (R)-enantiomer 4-[(5R)-6,7-dihydro-5H-pyrrolo[1,2-c]imidazol-5-yl]-3-fluorobenzonitrile to at least 50%, more preferably to at least 70%, even more preferably to at least 90%, even more preferably to at least 95%, even more preferably to at least 98% based on the total amount to the compound 4-[6,7-dihydro-5H-pyrrolo[1,2-c]imidazol-5-yl]-3-fluorobenzonitrile in the pharmaceutical dosage form.

In the aspects of the present invention the drug substance is in its free form or in the form of any pharmaceutically acceptable salt, complex, co-crystal, hydrate or solvate thereof.

In one embodiment compound of formula (1) is present in its free base form.

In another embodiment compound of formula (1) is present as phosphate salt; in yet another embodiment as mono-phosphate salt; in yet another embodiment as anhydrous mono-phosphate salt (1:1 molar ratio of compound of formula (1) and phosphate. The mono-phosphate salt is also referred to as dihydrogen phosphate.

In one embodiment, compound of formula (1) is present as anhydrous mono-phosphate salt in a polymorphic form characterized by an XRPD (X-ray powder diffraction) pattern comprising at least one or all of the following characteristic peaks (2-theta, angle of refraction, ±0.2°): 12.9°, 16.3°, 20.4°. Said polymorphic form is described in WO2013/109514 A1 as "Form A". The latter disclosure provides the process for preparing this form and further details on the characterization of this form (Example 1) and is incorporated herein as reference.

In the aspects of the present invention the drug substance is present in the pharmaceutical dosage form, calculated based on its free base, from 0.5 to 20%, preferably from 0.5 to 10%, more preferably from 1-8%, even more preferably 4±1% by weight based on the total weight of said pharmaceutical dosage form.

In the aspects of the present invention the pharmaceutical dosage form comprises microcrystalline cellulose, Ph. Eur., USP/NF, JP. The embodiments of the present invention said MCC is present to at least 30%, 30 to 95%, 40 to 95%, 50 to 95%, 60 to 95%, 70 to 95%, 30 to 90%, 40 to 90%, 50 to 90%, 60 to 90%, 70 to 90%, 30 to 85%, 40 to 85%, 50 to 85%, 80 to 85%, or 70 to 85%. In a preferred embodiment MCC is present from 30 to 95%, in a more preferred embodiment from 50 to 90%, in an even more preferred embodiment from 70 to 85%, in an even more preferred embodiment 77±7% by weight based on the total weight of said pharmaceutical dosage form.

The MCC may have a mean particle size of 30-300 micron, 45-180 micron, 70-130 micron, or 100±15 micron as measured by laser diffraction, said particle size being measured by laser light diffraction.

The MCC may have a loose bulk density of 0.2-0.5 g/mL, 0.25-0.4 g/mL or 0.31±0.03 g/mL.

In the exemplified embodiments the MCC has a mean particle size of 100±15 micron and a loose bulk density of 0.31±0.03 g/mL. Said quality of MCC is commercially available as Avicel PH 102 from FMC BioPolymer (Nominal particle size 100 micron; moisture 3.0 to 5.0%; loose bulk density 0.28-0.33 g/cc) or Vivapur 102 from JRS Pharma (JRS=J. Rettenmaier & Söhne; average particle size by laser diffraction 100 micron; bulk density 0.28-0.33 g/cm$^3$) and is herein also referred to as cellulose MK GR. This quality provides good tablet properties, e.g. good tablet hardness.

The advantages of the use of MCC in the composition of a pharmaceutical dosage form comprising the drug substance compound of formula (1) is that there are no chemical degradation reactions as observed for lactose, and no stickiness issues and no discoloration issues as observed for mannitol. Further, the advantage of MCC is that it transforms the very cohesive drug substance, particularly the very cohesive phosphate salt of compound of formula (1) into a pharmaceutically well processable blend material. For example, without MCC the drug substance can not be sieved through, e.g. through a 0.8 mm screen, although its primary particle size (ca. 4 micron) is smaller than the screen size. Due to the high tendency to aggregate the drug substance forms larger secondary particle agglomerates (up to 1 mm size) which do not pass the sieve any longer. However, if for example the phosphate salt of the drug substance of compound of formula (1) is blended with MCC in a weight ratio (weight of compound of formula (1) as mono-phosphate salt:weight of MCC) of ca. 1:1, ca. 1:1.5, ca. 1:2, ca. 1:5, ca. 1:6, or with more MCC, a blend material is obtained which can be easily sieved through a 0.8 mm screen.

The pharmaceutical dosage forms according to present invention may further comprise a glidant, preferably it comprises a glidant, preferably said glidant is a silicon dioxide, more preferably said glidant is a colloidal silicon dioxide, Ph. Eur., USP/NF, JP.

There is further provided the pharmaceutical dosage form according to present invention wherein said glidant is present from 0.1 to 5%, preferably 0.3 to 1.5%, more preferably 0.6±0.3% by weight based on the total weight of said pharmaceutical dosage form.

Preferably said glidant is a colloidal silicon dioxide, also referred to as hydrophilic fumed silica, with a surface area by BET of 200±25 m$^2$/g, e.g. such as it is commercialized under the tradename Aerosil 200 Pharma by Evonik (formerly Degussa; BET surface area 200±25 m$^2$/g; loss on drying ≤2.5 wt. %; pH 3.5-5.5).

The inventors of the present invention experienced occasionally capping issues (top of the tablet, i.e. the upper cap, splits along the edge of the cap and band of the tablet) and low tablet hardness values with tablets of the phosphate salt of the drug substance compound of formula (1) when those tablets were produced without a glidant or with only low levels of glidant (ca. 0.2% only). However, with ca. 0.5% by weight of the glidant colloidal silicon dioxide based on the total final blend ready for tablet compression, the capping tendency was eliminated even at high compression force and the tablet hardness values were significantly increased. Therefore, the presence of a glidant in a pharmaceutical composition of the compound of formula (1) has advantages, particularly when said glidant is present extragranularly.

In accordance with the present invention, there is provided the use of colloidal silicon dioxide to prevent capping issues with tablets comprising the drug substance 4-[(5R)-6,7-dihydro-5H-pyrrolo[1,2-c]imidazol-5-yl]-3-fluorobenzonitrile.

In a preferred embodiment, the pharmaceutical dosage form according to the present invention comprises
  (a) the drug substance 4-[(5R)-6,7-dihydro-5H-pyrrolo[1,2-c]imidazol-5-yl]-3-fluorobenzonitrile or any pharmaceutically acceptable salt thereof, preferably said drug substance is present as phosphate salt, more preferably as mono-phosphate salt,
  (b) at least 30% by weight of microcrystalline cellulose based on the total weight of said pharmaceutical dosage form, and
  (c) a glidant, preferably said glidant is colloidal silicon dioxide.

In a more preferred embodiment, the pharmaceutical dosage form according to the present invention comprises:
  (a) 0.5-20%, calculated based on its free base, by weight of the drug substance 4-[(5R)-6,7-dihydro-5H-pyrrolo[1,2-c]imidazol-5-yl]-3-fluorobenzonitrile present as monophosphate salt,
  (b) 30-95% by weight of the microcrystalline cellulose,
  (c) 0.1-5% by weight of the colloidal silicon dioxide,
  based on the total weight of said pharmaceutical dosage form.

In a more preferred embodiment, the pharmaceutical dosage form according to the present invention comprises:
  (a) 0.5-20%, calculated based on its free base, by weight of the drug substance 4-[(5R)-6,7-dihydro-5H-pyrrolo[1,2-c]imidazol-5-yl]-3-fluorobenzonitrile present as monophosphate salt,
  (b) 30-95%, 50-95%, 70-90%, or 80±5% by weight of the microcrystalline cellulose,
  (c) 0.1-5% by weight of the colloidal silicon dioxide, based on the total weight of said pharmaceutical dosage form.

More specifically, in preferred embodiments of the present invention, the pharmaceutical dosage comprises an internal phase (also referred to as intragranular phase) and an external phase (also referred to as extragranular phase), wherein the internal phase comprises:
  (a) 0.5-20%, preferably 5-15%, more preferably 10±2%, calculated based on its free base, by weight of the drug substance 4-[(5R)-6,7-dihydro-5H-pyrrolo[1,2-c]imidazol-5-yl]-3-fluorobenzonitrile present as monophosphate salt, and
  (b) 50-95%, preferably 70-90%, more preferably 80±5% by weight of the microcrystalline cellulose,
  based on the total weight of internal phase, and
and wherein the external phase comprises:
  (c) 0.1-5%, preferably 0.2-1%, more preferably 0.5±5% by weight of the colloidal silicon dioxide,
  based on the total weight of the final blend.

In preferred embodiments of the present invention, the pharmaceutical dosage comprises an internal phase (also referred to as intragranular phase) and an external phase (also referred to as extragranular phase), wherein the internal phase comprises:
  (a) 5-15%, calculated based on its free base, by weight of the drug substance 4-[(5R)-6,7-dihydro-5H-pyrrolo[1,2-c]imidazol-5-yl]-3-fluorobenzonitrile present as monophosphate salt, and
  (b) 70-90% by weight of the microcrystalline cellulose,
  based on the total weight of internal phase, and
and wherein the external phase comprises:
  (c) 0.1-5% by weight of the colloidal silicon dioxide,
  based on the total weight of the final blend.

In more preferred embodiments of the present invention, the pharmaceutical dosage comprises an internal phase (also referred to as intragranular phase) and an external phase (also referred to as extragranular phase), wherein the internal phase comprises:
  (a) 5-15%, calculated based on its free base, by weight of the drug substance 4-[(5R)-6,7-dihydro-5H-pyrrolo[1,2-c]imidazol-5-yl]-3-fluorobenzonitrile present as monophosphate salt, and
  (b) 70-90% by weight of the microcrystalline cellulose,
  based on the total weight of internal phase, and
and wherein the external phase comprises:
  (c) 0.2-1% by weight of the colloidal silicon dioxide,
  based on the total weight of the final blend.

The terms internal phase or intragranular phase refer to that part of the composition which is granulated (e.g. by wet granulation) or compacted (e.g. by roller compaction).

The terms external phase or extragranular phase refer to that part of the composition which is added to the granulated or compacted internal phase to make up together with said internal phase the final blend.

The term final blend refers to the combined internal and external phase which is ready for being compressed to tablets or filled into capsules.

The pharmaceutical dosage form according to present invention may further comprise mannitol, preferably it further comprises mannitol, more preferably it comprises mannitol in the external phase.

In preferred embodiments of the present invention, said mannitol is present in the pharmaceutical dosage form from 3 to 40%, preferably 5 to 40%, more preferably 5 to 15%, even more preferably 10±2% by weight based on the total weight of said pharmaceutical dosage form.

More specifically, in preferred embodiments of the present invention, said mannitol in said amounts is present in the external phase.

Preferably said mannitol is in a quality suitable for direct compression (herein also referred to as mannitol DC), e.g. Parteck M 200 by Merck.

In a particularly preferred embodiment of the present invention the pharmaceutical dosage form comprises:
(a) 1-8%, preferably 4±1%, calculated based on its free base, by weight of the drug substance 4-[(5R)-6,7-dihydro-5H-pyrrolo[1,2-c]imidazol-5-yl]-3-fluorobenzonitrile present as monophosphate salt,
(b) 30-90%, preferably 77±7% by weight of the microcrystalline cellulose,
(c) 0.1-5%, preferably 0.8±0.3% by weight of the colloidal silicon dioxide, and
(d) 5-40%, preferably 10±2% by weight of mannitol; optionally further comprising:
(e) 0.1-5%, preferably 2±0.5% by weight of a disintegrant, preferably croscarmellose sodium (herein also referred to as Na-CMC XL), e.g. Ac-Di-Sol by FMC BioPolymer), and
(f) 0.1-3%, preferably 1.5±0.5% by weight of a lubricant, preferably magnesium stearate.
based on the total weight of said pharmaceutical dosage form The pharmaceutical dosage form according to present invention may be in the form of a powder, capsule, or tablet, preferably it is in the form of a tablet.

In a preferred embodiment of the present invention the pharmaceutical dosage form is in the form of a tablet and the tablet is coated with a film, i.e. a film-coated tablet, preferably said film comprises polyvinyl alcohol and optionally, plasticizer and pigment (e.g. Opadry Premix by Colorcon).

In accordance with the second aspect of the present invention there is provided a process for the preparation of the pharmaceutical dosage forms as described before herein comprising blending the drug substance 4-[(5R)-6,7-dihydro-5H-pyrrolo[1,2-c]imidazol-5-yl]3-fluorobenzonitrile with microcrystalline cellulose (MCC).

Preferably said blending of the drug substance with MCC is performed as a first process step before any sieving, screening, compaction, or compression step.

Said blending of the drug substance with MCC may be performed with MCC as the only excipient or with MCC in combination with a glidant, preferably colloidal silicon dioxide, and optionally with a disintegrant.

Preferably said process further comprises the use of a glidant to prepare a blend which is ready for tabletting.

In preferred embodiments of the present inventions, said process is further characterized by the following process steps:
(1) blending the drug substance 4-[(5R)-6,7-dihydro-5H-pyrrolo[1,2-c]imidazol-5-yl]-3-fluorobenzonitrile together with microcrystalline cellulose, and optionally further ingredients such as colloidal silicon dioxide, a disintegrant, preferably croscarmellose, and a lubricant, preferably magnesium stearate (said ingredients make up the internal phase), to obtain a machine-compactable blend,
(2) compacting the machine-compactable blend by dry granulation, preferably by roller compaction, to obtain a compacted material,
(3) blending the compacted material with colloidal silicone dioxide, and optionally with further ingredients such as fillers, preferably microcrystalline cellulose, and/or mannitol more preferably microcrystalline cellulose and mannitol, a disintegrant, preferably croscarmellose sodium, and a lubricant, preferably magnesium stearate (said ingredients make up the external phase), to obtain a machine-compressible blend (also referred to as final blend),
(4) compressing the machine-compressible blend by use of a tabletting machine to obtain tablets.

In a particularly preferred embodiment, the process is further characterized by the following process steps:
(1) blending the drug substance 4-[(5R)-6,7-dihydro-5H-pyrrolo[1,2-c]imidazo-5-yl]-3-fluorobenzonitrile together with microcrystalline cellulose, colloidal silicon dioxide, and a disintegrant, preferably croscarmellose, to obtain a blend,
(2) screening the blend of step (2), preferably through 0.5-2 mm, more preferably 0.6-1.0 mm, even more preferably 0.8 mm,
(3) blending the screened blend of step (3) with a lubricant, preferably magnesium stearate, to obtain a machine-compactable blend,
(4) compacting the machine-compactable blend of step (3) by dry granulation, preferably by roller compaction,
(5) screening the compacted blend of step (4), preferably through 0.5-2 mm, more preferably 0.6-1.0 mm, even more preferably 0.8 mm,
(6) blending the screened compacted material of step (5) with microcrystalline cellulose, colloidal silicone dioxide, mannitol, and a disintegrant, preferably croscarmellose sodium, to obtain a blend,
(7) blending the blend of step (6) with a lubricant, preferably magnesium stearate, to obtain a machine-compressible blend,
(8) compressing the machine-compressible blend of step (7) by use of a tabletting machine to obtain core tablets,
(9) coating of the core tablets of step (8) to obtain film coated tablets.

In accordance with the third aspect of the present invention, there are provided the pharmaceutical dosage forms obtainable by any of the process embodiments as described before herein.

In accordance with the fourth aspect of the invention, there is provided the use of microcrystalline cellulose to transform the drug substance 4-[(5R)-6,7-dihydro-5H-pyrrolo[1,2-c]imidazol-5-yl]-3-fluorobenzonitrile into a pharmaceutically processable material.

In accordance with a fifth aspect of the invention, there is provided the use of colloidal silicon dioxide to prevent capping issues with tablets comprising the drug substance 4-[(5R)-6,7-dihydro-5H-pyrrolo[1,2-c]imidazol-5-yl]-3-fluorobenzonitrile.

In accordance with a sixth aspect of the invention, there is provided a pharmaceutical dosage form for use in treating Cusing's disease or Cushing's syndrome.

In accordance with a seventh aspect of the invention, there is provided a method of treating Cusing's disease or Cushing's syndrome, comprising the step of administering a therapeutically effective amount of pharmaceutical dosage form to a patient suffering from said disease.

EXAMPLES

Example 1: Tablet Manufacturing

The manufacturing of film-coated tablets of drug substance compound of formula (1) mono-phosphate salt is performed according to the composition as displayed in Table 1 below. The same composition is used to manufacture tablets in dosage strength of 5 mg, 10 mg, and 20 mg.

The core tablets manufacture consists of dry granulation, sizing, blending and tabletting steps:

1. Add approximately 50% of the internal phase microcrystalline cellulose (part 1) into suitable container and add the full amount of drug substance followed by remaining the 50% of internal phase microcrystalline cellulose (part 2), Na-CMC-XL and Aerosil to get a sandwich of drug substance between two layers of excipients; blend the mixture in a diffusion mixer.
2. Screen the blend from step 1 through a screening mill with oscillating bar (Frewilt MGW 520/6, 0.8 mm screen, round wire, 57-104 rpm).
3. Sieve Magnesium stearate (hand sieve, screen size 0.8 mm) and add it to the material from step 2 and blend the combined materials in a diffusion mixer.
4. Compact blend from step 3 in a dry granulator, e.g. a roller compactor (Roller Bepex Hosokawa Pharmapaktor L-200/30P, 18 kN compaction force, 3-6 rpm roller speed (revolution compaction roll), revolution screw speed to be adapted to the compaction force).
5. Sieve compacted material from step 4 with a screening mill with oscillating bar (Frewitt MGW 520/6, 0.8 mm screen, round wire, 57-104 rpm).
6. Sieve Microcrystalline Cellulose, Mannitol, Na-CMC-XL and Aerosil (hand sieve, 0.8 mm screen size) and add it to material from step 5 and blend in a diffusion mixer.
7. Sieve Magnesium stearate (hand sieve, 0.8 mm screen size) and add it to the material from step 6 and blend the combined materials in a diffusion mixer.
8. Compress the final blend from step 7 using a rotary tabletting machine (FETTE 1200i TP09, 8 Euro B punches, compression force setting 1-40 kN to meet target hardness of 80 N for 5 mg tablet, 100 N for 10 mg tablet, 160 N for 20 mg tablet).
9. Coat the core tablet from step 8 in a perforated pan coater (Glatt GC 750 or 1000).

A common final blend for different dosage strengths can be manufactured by running a common granulation and blending. The final blend is split according to the final core tablet batch size per dosage strength and compressed on a tablet press to yield the final core tablet.

The resulting tablet cores are coated in a side vented, perforated coating pan with a standard aqueous coating suspension.

TABLE 1

Formula for all dosage strength in the range 5-20 mg, composition and batch quantity for 10 mg dosage strength tablets are given as representative examples, internal and external phase ingredients separately listed

| Component | Composition of internal phase [%] | Composition of core tablet [%] | Composition of film-coated tablet [%] | Composition of 10 mg tablet [mg] | Quantity per 45.0 kg batch for 10 mg tablets [kg] |
|---|---|---|---|---|---|
| Internal Phase | | | | | |
| Compound of formula (1) as mono-phosphate salt[a] (corresponds to compound of formula (1) as free base) | 14.31[a] (10.00) | 6.36[a] (4.44) | 6.12[a] (4.27) | 14.310[a] (10.000) | 2.862[a] |
| Cellulose MK GR | 82.19 | 36.53 | 35.12 | 82.190 | 16.438 |
| Aerosil 200 PH | 0.50 | 0.22 | 0.21 | 0.500 | 0.100 |
| Na-CMC-XL | 2.00 | 0.89 | 0.85 | 2.000 | 0.100 |
| Magnesium stearate | 1.00 | 0.44 | 0.43 | 1.000 | 0.200 |
| Internal Phase Weight | 100.00 | | | 100.000 | |
| External Phase | | | | | |
| Cellulose MK GR | | 43.06 | 41.39 | 96.860 | 19.372 |
| Mannitol DC | | 10.00 | 9.62 | 22.500 | 4.500 |
| Aerosil 200 PH | | 0.50 | 0.48 | 1.120 | 0.224 |
| Na-CMC-XL | | 1.00 | 0.97 | 2.260 | 0.452 |
| Magnesium stearate | | 1.00 | 0.97 | 2.260 | 0.452 |
| Final Blend Weight, Core Tablet Weight | | 100.00 | | 225.000 | 45.000 |
| Coating pre-mix | | | 3.85 | 9.000 | 1.800 |
| Dyes | | | 3.85 | 9.000 | 1.800 |
| Purified water[b] | | | — | — | 10.200[b] |
| Film Coated Tablet Weight | | | 100.00 | 234.000 | 46.800 |

[a]The salt factor is 1.431. The drug substance quantity has to be adjusted if the content is ≤99.5%. Respective compensation is done by adjusting the Cellulose MK GR content.
[b]The water used during granulation is removed in the process of drying.

TABLE 2

Formula for all dosage strength in the range 5-20 mg, composition and batch quantity for 10 mg dosage strength tablets are given as representative examples, internal and external phase ingredients listed as combined values

| Component | Composition of core tablet [%] | Composition of film-coated tablet [%] | Composition of 10 mg tablet [mg] | Quantity per 46.0 kg batch for 10 mg tablets [kg] |
|---|---|---|---|---|
| Compound of formula (1) as mono-phosphate salt[a] (corresponds to compound of formula (1) as free base) | 6.36[a] (4.44) | 6.12[a] (4.27) | 14.310[a] (10.000) | 2.862[a] |
| Cellulose MK GR | 79.59 | 76.51 | 179.050 | 35.810 |
| Mannitol DC | 10.00 | 9.62 | 22.500 | 4.500 |
| Aerosil 200 PH | 0.72 | 0.61 | 1.620 | 0.324 |
| Na-CMC-XL | 1.89 | 1.82 | 4.260 | 0.852 |
| Magnesium stearate | 1.44 | 1.40 | 3.260 | 0.652 |
| Core Tablet Weight | 100.0% | | 225.00 | 45.000 |
| Coating pre-mix | | 3.85 | 9.000 | 1.800 |
| Dyes | | 3.85 | 9.000 | 1.800 |
| Purified water[b] | — | — | | 10.200[b] |
| Film Coated Tablet Weight | | 100% | 234.000 | 46.800 |

[a]The salt factor is 1.431. The drug substance quantity has to be adjusted lithe content is ≤99.5%. Respective compensation is done by adjusting the Cellulose MK GR content.
[b]The water used during granulation is removed in the process of drying.

TABLE 3

Specifications and in-process controls (IPC) for 5 mg, 10 mg, and 20 mg core tablets

| | 5 mg core tablet [%] | 10 mg core tablet [%] | 20 mg core tablet [%] |
|---|---|---|---|
| Weight (20 tablets) | 112.5 mg ± 15% | 225.0 mg ± 15% | 450 mg ± 10% |
| Shape | round | round | round |
| Diameter | 7 mm | 9 mm | 11 mm |
| Thickness (20 tablets) | 2.8 ± 0.3 mm | 3.4 ± 0.3 mm | 4.4 ± 0.3 mm |
| Hardness (20 tablets, target, range of mean) | 80 ± 20N | 100 ± 20N | 160 ± 30N |
| Friability (6.5 g tablets) | No breakage ≤0.8% abrasion | No breakage ≤0.8% abrasion | No breakage ≤0.8% abrasion |
| Disintegration time (6 units, without disc, water, 37° C.) | <15 min | <15 min | <15 min |

TABLE 4

Specifications and in-process controls (IPC) for 5 mg, 10 mg, and 20 mg film-coated tablets

| | 5 mg film-coated tablet [%] | 10 mg film-coated tablet [%] | 20 mg film-coated tablet [%] |
|---|---|---|---|
| Weight (20 tablets) | 118.00 mg ± 15% | 234.00 ± 15% | 446.00 mg ± 10% |
| Shape | round | round | round |
| Diameter | 6.9-7.3 mm | 8.9-9.3 mm | 10.9-11.3 mm |
| Thickness (20 tablets) | 2.9-0.3 mm | 3.5-0.3 mm | 4.5-0.3 mm |
| Friability (6.5 g tablets) | No breakage | No breakage | No breakage |
| Disintegration time (6 units, without disc, water, 37° C.) | <15 min | <15 min | <15 min |

The invention claimed is:

1. A method of treating Cushing's disease or Cushing's syndrome with a pharmaceutical dosage form for oral administration comprising: (a) a drug substance 4-[(5R)-6,7-dihydro-5H-pyrrolo[1,2-c]imidazol-5-yl]3-fluorobenzonitrile as defined by formula (1)

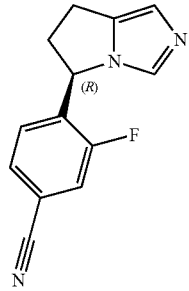

(1)

or any pharmaceutically acceptable salt thereof, and (b) 70% to 95% by weight of microcrystalline cellulose based on the total weight of said pharmaceutical dosage form.

2. The method according to claim 1, wherein the drug substance is present as phosphate salt.

3. The method according to claim 2, wherein the drug substance is present as a mono-phosphate sa it.

4. The method according to claim 1, wherein the drug substance, calculated based on its free base, is present from 0.5 to 20% by weight based on the total weight of said pharmaceutical dosage form.

5. The method according to claim 1, wherein 4-[(5R)-6,7-dihydro-5H-pyrrolo[1,2-c]imidazol-5-yl]-3-fluorobenzonitrile or any pharmaceutically acceptable salt thereof is combined with 70% to 95% by weight of microcrystalline cellulose based on the total weight of said pharmaceutical dosage form into a pharmaceutically processable material to provide the pharmaceutical dosage form for oral administration.

* * * * *

UNITED STATES PATENT AND TRADEMARK OFFICE
CERTIFICATE OF CORRECTION

PATENT NO. : 10,709,691 B2
APPLICATION NO. : 16/175082
DATED : July 14, 2020
INVENTOR(S) : Stefania Beato and Peggy Quinton Page 1 of 1

It is certified that error appears in the above-identified patent and that said Letters Patent is hereby corrected as shown below:

In the Claims

Column 12, Claim 3, Line 65: sa it should read salt.

Signed and Sealed this
Twenty-seventh Day of October, 2020

Andrei Iancu
*Director of the United States Patent and Trademark Office*